US009558336B2

(12) United States Patent
Lee

(10) Patent No.: US 9,558,336 B2
(45) Date of Patent: Jan. 31, 2017

(54) PERSISTENT AUTHENTICATION USING SENSORS OF A USER-WEARABLE DEVICE

(71) Applicant: Salutron, Inc., Fremont, CA (US)

(72) Inventor: Yong Jin Lee, Palo Alto, CA (US)

(73) Assignee: SALUTRON INC., Newark, CA (US)

( * ) Notice: Subject to any disclaimer, the term of this patent is extended or adjusted under 35 U.S.C. 154(b) by 0 days.

(21) Appl. No.: 14/505,189

(22) Filed: Oct. 2, 2014

(65) Prior Publication Data
US 2015/0135310 A1 May 14, 2015

Related U.S. Application Data

(60) Provisional application No. 61/886,930, filed on Oct. 4, 2013.

(51) Int. Cl.
*G06F 21/32* (2013.01)
*A61B 5/00* (2006.01)
*G06F 1/16* (2006.01)
*G06F 21/35* (2013.01)
*G06F 21/34* (2013.01)
*A61B 5/0452* (2006.01)

(52) U.S. Cl.
CPC .............. *G06F 21/32* (2013.01); *A61B 5/0452* (2013.01); *A61B 5/681* (2013.01); *G06F 1/163* (2013.01); *G06F 21/34* (2013.01); *G06F 21/35* (2013.01); *G06F 2221/2135* (2013.01)

(58) Field of Classification Search
CPC .......... G06F 21/31; G06F 21/32; G06F 21/35; G06F 21/60; G06K 19/0775; H04L 63/0823
USPC ...................................... 726/5–7, 16, 20, 26
See application file for complete search history.

(56) References Cited

U.S. PATENT DOCUMENTS

| 7,689,833 | B2 |   | 3/2010 | Lange |              |
|-----------|----|---|--------|---------|--------------|
| 9,111,085 | B1 | * | 8/2015 | Darmour | G06F 21/35   |
| 9,112,701 | B2 | * | 8/2015 | Sano    | H04L 9/32    |
| 9,276,541 | B1 | * | 3/2016 | Froment | H03G 3/20    |

(Continued)

OTHER PUBLICATIONS

Bionym, NYMI Preorder Your Nymi Now, Nov. 2013, https://www.getnymi.com/preorder/.

(Continued)

*Primary Examiner* — Hadi Armouche
*Assistant Examiner* — Hee Song
(74) *Attorney, Agent, or Firm* — Vierra Magen Marcus LLP

(57) ABSTRACT

A user-wearable device includes a housing and a band that straps the housing to a portion of a user's body (e.g., wrist). One or more skin contact sensors in and/or on the housing can sense biometric information of a user wearing the device. An authentication module performs or receives results of an authentication determination that compares the sensed biometric information to baseline biometric information to determine whether they match. An on-body detector uses one or more of the sensors to determine whether the device is being worn by a user. After a user is authenticated based on a match between the sensed and baseline biometric information, the authentication module continually concludes that the user is authenticated for at least a period of time, without an additional comparison between sensed and baseline biometric information, if the on-body detector detects that the user-wearable device is still being worn by the user.

18 Claims, 12 Drawing Sheets

(56) References Cited

U.S. PATENT DOCUMENTS

| | | |
|---|---|---|
| 2003/0025603 A1 | 2/2003 | Smith |
| 2011/0172500 A1* | 7/2011 | Van Dooren ............ A61B 5/16 600/300 |
| 2011/0214158 A1* | 9/2011 | Pasquero ................ G06F 21/35 726/2 |
| 2013/0120106 A1 | 5/2013 | Cauwels et al. |
| 2014/0143785 A1* | 5/2014 | Mistry .................. G06F 9/4893 718/104 |
| 2014/0188770 A1* | 7/2014 | Agrafioti ................ A61B 5/117 706/13 |
| 2014/0308930 A1* | 10/2014 | Tran ...................... H04W 4/001 455/414.1 |
| 2014/0366123 A1* | 12/2014 | DiBona .................. G06F 21/60 726/16 |
| 2014/0372762 A1* | 12/2014 | Flautner ................ H04L 9/3226 713/173 |
| 2015/0058942 A1* | 2/2015 | Dermu .................. G06F 21/445 726/6 |
| 2015/0366469 A1* | 12/2015 | Harris .................. A61B 5/0245 600/301 |

OTHER PUBLICATIONS

Stinson, This Little Wristband Will Replace Your Passwords With Your Heartbeat, Sep. 11, 2013, http://www.wired.com/2013/09/this-little-wristband-wants-to-replace-your-passwords-and-keys-with-your-heartbeat/.

Bionym, The NYMI, White Paper, Nov. 19, 2013, http://www.getnymi.com/wp-content/uploads/2013/11/NymiWhitePaper-1.pdf.

International Search Report & The Written Opinion of the International Searching Authority dated May 12, 2015, International Application No. PCT/US2014/059049.

International Preliminary Report on Patentability dated Apr. 5, 2016, in International Application No. PCT/US2014/059049.

* cited by examiner

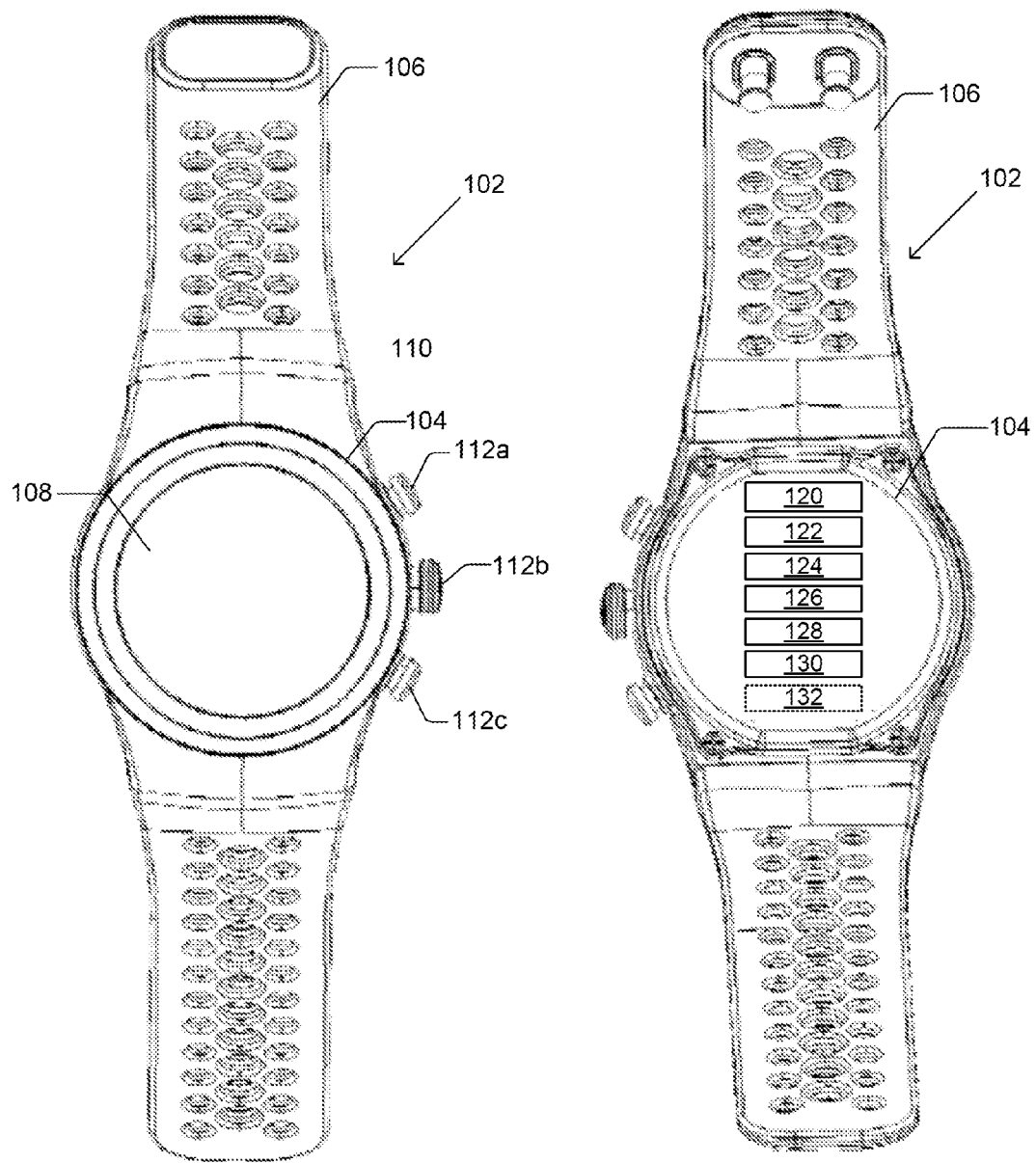
*FIG. 1A*  *FIG. 1B*

PERSISTENT AUTHENTICATION USING SENSORS OF A USER-WEARABLE DEVICE

PRIORITY CLAIM

The present application claims priority to U.S. Provisional Patent Application No. 61/886,930, filed Oct. 4, 2013, which is incorporated herein by reference.

BACKGROUND

Authentication of a user's identity involves verifying a user is who he or she represents himself or herself to be or has credentials, typically for accessing data or a service. Authentication is particularly useful in computer security to prevent a user from accessing data available via a computer system but for which the user does not have access permission. Biometric authentication techniques may be used. Authentication may be desired on a continuous basis and in a manner which does not interrupt the user's activity in interfacing with an application, computer system or machine controlled by a computer system. For example, distraction caused by interrupting a user to re-enter a password or put his or her eye to a retinal scanning device while engaged in an activity is to be avoided.

BRIEF DESCRIPTION OF THE DRAWINGS

FIG. 1A depicts a front view of a user-wearable device, according to an embodiment.

FIG. 1B depicts a rear view of the user-wearable device of FIG. 1A, according to an embodiment.

DETAILED DESCRIPTION

Figure 1C:
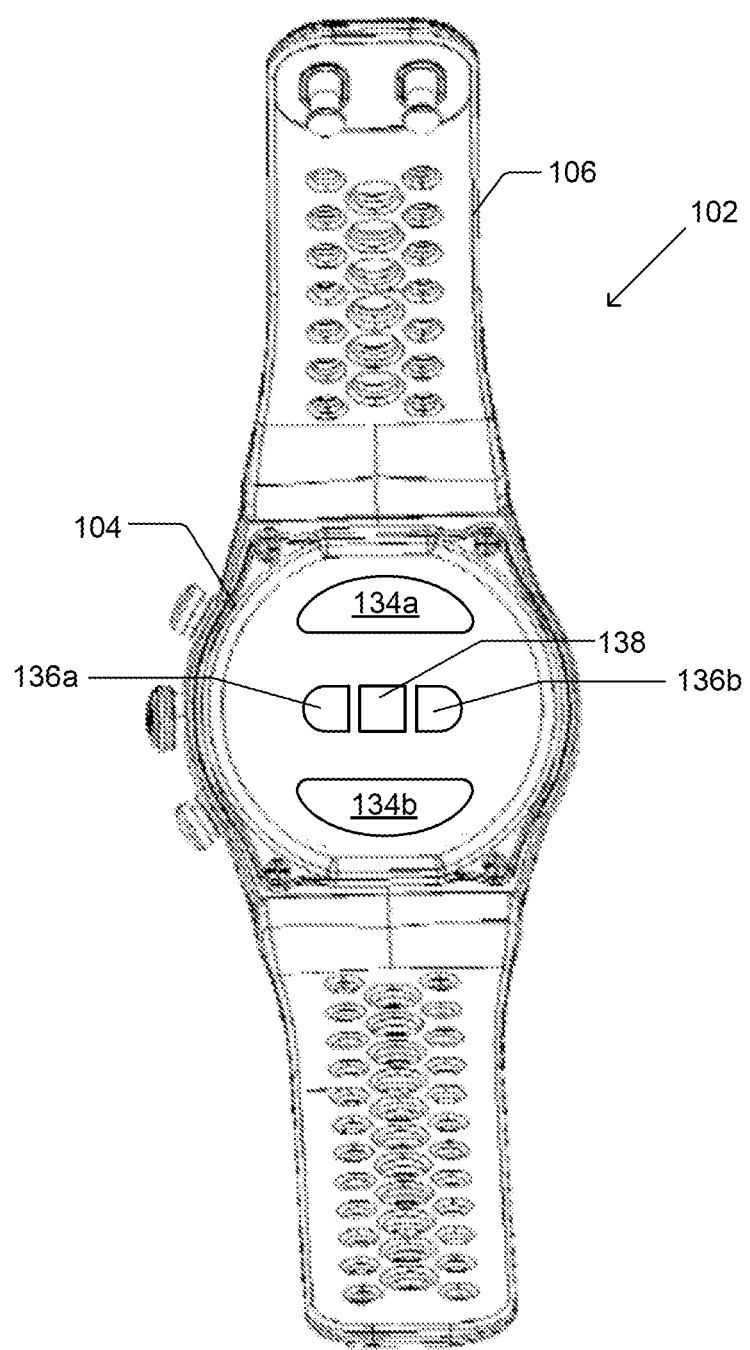
FIG. 1C depicts a specific implementation of contact sensors that are viewable from the rear or caseback of the user-wearable device of FIGS. 1A and 1B, according to an embodiment.

In the following detailed description, reference is made to the accompanying drawings that form a part hereof, and in which is shown by way of illustration specific illustrative embodiments. It is to be understood that other embodiments may be utilized and that mechanical and electrical changes may be made. The following detailed description is, therefore, not to be taken in a limiting sense. In the description that follows, like numerals or reference designators will be used to refer to like parts or elements throughout. In addition, the first digit of a reference number identifies the drawing in which the reference number first appears.

Besides security of computer access and data stored by a computer system, biometric authentication may also come in useful in other contexts to verify someone was at a place or is performing an activity such as exercise. Continuous authentication may also be useful, for example in military or other environments requiring high security or monitoring of activity over time. For example, during operations where exposures to chemical and biological threats are possible, a warfighter wears a Military Oriented Protective Posture (MOPP) suit. To allow the warfighter secure and efficient access to networked workstations, continuous authentication of the warfighter in the MOPP suit is desired. Additionally, a user-wearable device (e.g., a wearable wrist contact sensor device, such as a watch or other device—but not limited to a watch) communicating with a base station (e.g., computer, smart phone, tablet, laptop, or other computing device) can provide authentication without explicit intervention from a user wearing the user-wearable device. In another example, a user may be exercising on a machine and his or her user-wearable device (e.g., wrist contact sensing device) continuously authenticates the user based on his or her wrist vein pattern. A pulse or other sensor reading in a military context may insure the wearer of the device has not been killed and his wrist is being used post mortem. In an exercise or health monitoring situation, the additional pulse data can verify a health state of the user based on stored pulse data patterns representing various conditions or stored rules about changes reflected in the data.

The wrist is the carpus or joint between the forearm and the hand. Eight bones of the carpus and the distal ends of the radius and ulna form a complex articulation that allows three degrees of freedom. In order to provide the articulation while maintaining relative stability, the wrist has a complex configuration of ligaments linking the bones. The wrist also had a readily identifiable neurovascular structure. The primary pulsatile components in the wrist are the radial and ulnar arteries. The skin area of the wrist is sufficiently planar or flat so that sensors can be arranged in a planar or nearly planar configuration.

Technology is described for persistently authenticating a user. In an embodiment, a system automatically and continuously determines whether the user is wearing a user-wearable device (e.g., a wrist contact sensor device), automatically (and sometimes continuously) senses and registers biometric information (e.g., ECG and/or PPG data), determines whether the registered biometric information data matches pre-stored baseline biometric information and, if the registered biometric information matches the pre-stored baseline biometric information and the user is wearing the user-wearable device, concludes that the user is authenticated. When the user takes off the device, the user is no longer authenticated.

In accordance with an embodiment, a wrist based authentication system is based on the sensors used for multiparameter activity and wellness monitoring. For example, on one design the persistent authentication feature is based on detecting unique features of a subject's ECG and/or PPG signals in conjunction with a reliable, redundant detection of the removal of the device from the wrist. Additional details of ECG and PPG signals, as well as other types of information that can be sensed using sensors of a user-wearable device, are described below.

FIG. 1A depicts a front view of a user-wearable device 102, according to an embodiment, which can be used to provide for persistent authentication of a user that is wearing the user-wearable device. The user-wearable device 102 can be a standalone device which gathers and processes data and displays results to a user. Alternatively and preferably, the user-wearable device 102 can be capable of wirelessly communicating with a base station (252 in FIG. 2), which can be a mobile phone, a tablet computer, a personal data assistant (PDA), a laptop computer, a desktop computer, or some other computing device or system that is capable of performing wireless communication. The base station can, e.g., include a health and fitness software application and/or other applications, which can be referred to as apps. The user-wearable device 102 can upload data obtained by the device 102 to the base station, so that such data can be used by a health and fitness software application and/or other apps stored on and executed by the base station. Further, where the base station 252 is a mobile phone, the user-wearable device 102 can receive alerts or messages from the base station, which can be displayed to the user on the display 108. In certain embodiments, the user-wearable device 102 can also report to a base station, or more generally to any system external to the user-wearable device 102, whether a user that is wearing the user-wearable device 102 is authenticated.

The user-wearable device 102 is shown as including a housing 104, which can also be referred to as a case 104. A band 106 is shown as being attached to the housing 104, wherein the band 106 can be used to strap the housing 104 to a user's wrist or chest. Accordingly, the band 106 can also be referred to as a wristband. The housing 104 is shown as including a digital display 108, which can also be referred to simply as a display. The digital display 108 can be used to show the time, date, day of the week and/or the like. The digital display 108 can also be used to display activity and/or physiological metrics, such as, but not limited to, heart rate (HR), heart rate variability (HRV), calories burned, steps taken and distance walked and/or run. The digital display 108 can also be used to display sleep metrics, examples of which are discussed below. These are just examples of the types of information that may be displayed on the digital display 108, which are not intended to be all encompassing. The band 106, which can also be referred to as a strap because of its function, can be of different lengths than shown. For one example, a longer band 106 can be used to strap the user-wearable device 102 around a user's chest, rather than around a user's wrist. In other words, it is also within the scope of embodiments for the user-wearable device to be a device other than a wrist worn device.

The housing 104 is shown as including buttons 112a, 112b, 112c which can individually be referred to as a button 112, and can collectively be referred to as the buttons 112. For example, one of the buttons 112 can be a mode select button, while another one of the buttons 112 can be used to start and stop certain features. While the user-wearable device 102 is shown as including three buttons 112, more or less than three buttons can be included. The buttons 112 can additionally or alternatively be used for other functions. For example, one of the buttons 112 (e.g., 112b) can function as an electrode for the ECG sensor. It is also possible for a front facing electrode, for use by the ECG sensor, to be included on the housing 104.

Figure 2:
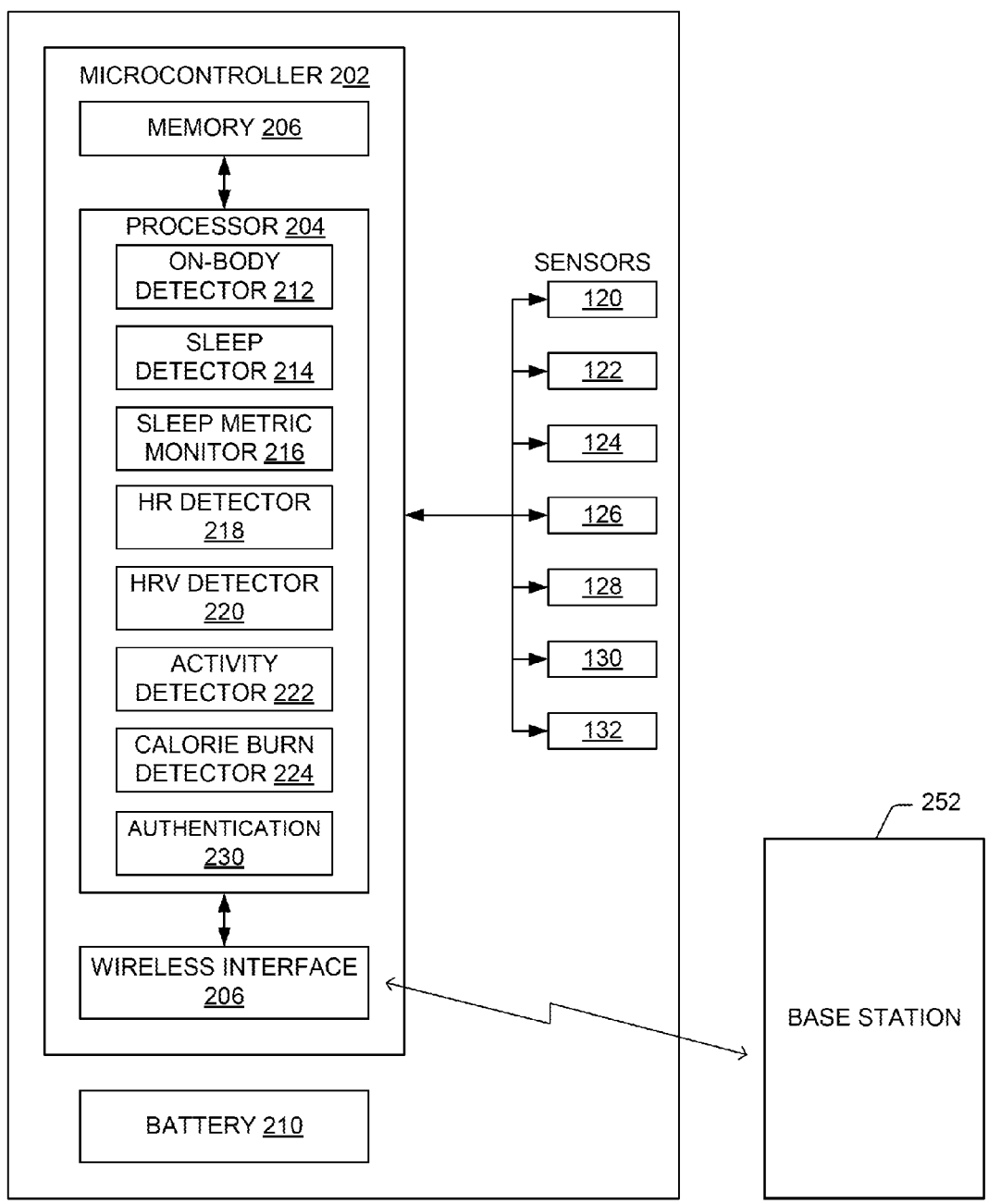
FIG. 2 depicts a high level block diagram of electrical components of the user-wearable device introduced in FIGS. 1A-1C, according to an embodiment.

As mentioned above, in certain embodiments, the user-wearable device 102 can receive alerts from a base station (e.g., 252 in FIG. 2). For example, where the base station 252 is a mobile phone, the user-wearable device 100 can receive alerts from the base station, which can be displayed to the user on the display 108. For a more specific example, if a mobile phone type of base station 252 is receiving an incoming phone call, then an incoming phone call alert can be displayed on the digital display 108 of the mobile device, which may or may not include the phone number and/or identity of the caller. Other types of alerts include, e.g., text message alerts, social media alerts, calendar alerts, medication reminders and exercise reminders, but are not limited thereto. The user-wearable device 102 can inform the user of a new alert by vibrating and/or emitting an audible sound. In certain embodiments, the user-wearable device 102 will only provide such alerts to a user wearing the device 102 if the user is authenticated.

FIG. 1B illustrates an exemplary rear-view of the housing or case 104 of the user-wearable device 102. Referring to FIG. 1B, the backside of the housing 104, which can also be referred to as a caseback, is shown as including a bioimpedance analysis (BIA) sensor, an optical sensor 122, a capacitive sensor 124, a galvanic skin resistance (GSR) sensor 126, an electrocardiogram (ECG) sensor 128 and a skin temperature sensor 130. It is also possible that the user-wearable device 102 includes less sensors than shown, more sensors than shown and/or alternative types of sensors. For example, the user-wearable device 102 can also include one or more type of motion sensor 132, which is shown in dotted line because it is likely completely encased with the housing 104.

In accordance with an embodiment, the bioimpedance analysis (BIA) sensor 120, which can include or connect to a pair of electrodes spaced apart from one another such that a patient's skin can complete a circuit between the electrodes, passes a current at a single frequency, or more preferably at multiple frequencies, through a user's tissue (proximate the sensor electrodes) and measures impedance. Based on these impedance measurements, algorithms, linear regression models and/or other mathematical modeling can be used to calculate the user's body water content and/or body fat percentage.

In accordance with an embodiment, the optical sensor 122 includes both a light source and a light detector, in which case the optical sensor 122 can be used to detect proximity of an object (e.g., a user's wrist or chest) relative to the optical sensor, as well as to detect ambient light. The light source of the optical sensor 122 can include one or more light emitting diode (LED), incandescent lamp or laser diode, but is not limited thereto. While infrared (IR) light sources are often employed in optical sensors, because the human eye cannot detect IR light, the light source can alternatively produce light of other wavelengths. The light detector of the optical sensor 122 can include one or more one or more photoresistor, photodiode, phototransistor, photodarlington or avalanche photodiode, but is not limited thereto. When operating as an optical proximity sensor, the light source of the optical sensor 122 is driven to emit light. If an object (e.g., a user's wrist or chest) is within the sense region of the optical sensor 122, a large portion of the light emitted by the light source will be reflected off the object and will be incident on the light detector. The light detector generates a signal (e.g., a current) that is indicative of the intensity and/or phase of the light incident on the light detector, and thus, can be used to detect the presence of the user's wrist or chest. The optical sensor 122 may also use its light detector to operate as an ambient light detector. It is also possible that the optical sensor 122 not include a light source, in which case the optical sensor 122 can operate as an ambient light sensor, but not a proximity sensor. When operating as an ambient light sensor, the optical sensor 122 produces a signal having a magnitude that is dependent on the amount of ambient light that is incident on the optical sensor 122. It is expected that when a user is wearing the user-wearable device 102 on their wrist or chest, the light detector of the optical sensor 122 will be blocked (by the user's wrist or chest) from detecting ambient light, and thus, the signal produced the light detector will have a very low magnitude.

In accordance with specific embodiments, the optical sensor 122 can also be used to detect heart rate (HR) and heart rate variability (HRV). More specifically, the optical sensor 122 can operate as a photoplethysmography (PPG) sensor. When operating as a PPG sensor, the light source of the optical sensor 122 emits light that is reflected or backscattered by patient tissue, and reflected/backscattered light is received by the light detector of the optical sensor 122. In this manner, changes in reflected light intensity are detected by the light detector, which outputs a PPG signal indicative of the changes in detected light, which are indicative of changes in blood volume. The PPG signal output by the light detector can be filtered and amplified, and can be converted to a digital signal using an analog-to-digital converter (ADC), if the PPG signal is to be analyzed in the digital domain. Each cardiac cycle in the PPG signal generally appears as a peak, thereby enabling the PPG signal to be used to detect peak-to-peak intervals, which can be used to calculate heart rate (HR) and heart rate variability (HRV). In accordance with certain embodiments, described below, a PPG signal sensed using the optical sensor 122 is used to determine whether or not to authenticate a user. In accordance with certain embodiments, the optical sensor 122 includes a light source that emits light of two different wavelengths that enables the optical sensor 122 to be used as a pulse oximeter, in which case the optical sensor 122 can non-invasively monitor the arterial oxygen saturation of a user wearing the user-wearable device 102.

In accordance with an embodiment, the capacitive sensor 124 includes or connects to an electrode that functions as one plate of a capacitor, while an object (e.g., a user's wrist or chest) that is in close proximity to the capacitive sensor 124 functions as the other plate of the capacitor. The capacitive sensor 124 can indirectly measure capacitance, and thus proximity, e.g., by adjusting the frequency of an oscillator in dependence on the proximity of an object relative to the capacitive sensor 124, or by varying the level of coupling or attenuation of an AC signal in dependence on the proximity of an object relative to the capacitive sensor 124.

The galvanic skin resistance (GSR) sensor 126, which can include or connect to a pair of electrodes spaced apart from one another such that a patient's skin can complete a circuit between the electrodes, senses a galvanic skin resistance. The galvanic skin resistance measurement will be relatively low when a user is wearing the user-wearable device 102 on their wrist or chest and the GSR sensor 126 is in contact with the user's skin. By contrast, the galvanic skin resistance measurement will be very high when a user is not wearing the user-wearable device 102 and the GSR sensor 126 is not in contact with the user's skin. The galvanic skin resistance measurement, which can also be referred to as a galvanic skin response, may also vary based on levels perspiration.

The ECG sensor 128 can be used to sense an ECG signal from a user that is wearing the user-wearable device 102 on their wrist or chest. If the user-wearable device 102 is worn on the user's wrist, then an ECG signal can be sensed when an electrode on the caseback of the housing 104 is in contact with the skin on the user's wrist, and the user's touches another electrode on the side (e.g., the button 112b) or front of the housing 104 using a finger on their other arm. If the user-wearable device 102 is worn on the user's chest, then an ECG signal can be sensed between two electrodes on the back of the housing 104 that are in contact with the skin on the user's chest. Additionally, or alternatively, electrodes of or connectable to the ECG sensor 128 can be incorporated into a chest strap that provides ECG signals to the user-wearable device 102.

The skin temperature sensor 130 can be implemented, e.g., using a thermistor, and can be used to sense the temperature of a user's skin, which can be used to determine user activity and/or calories burned.

Depending upon implementation, heart rate (HR) and heart rate variability (HRV) can be detected based on signals obtained by the optical sensor 122 and/or the ECG sensor 128. HR and/or HRV can be automatically determined continuously, periodically or at other specified times or based on a manual user action. For example, in a free living application, HR can be determined automatically during periods of interest, such as when a significant amount of activity is detected.

Additional physiologic metrics can also be obtained using the sensors described herein. For example, respiration rate can be determined from a PPG signal obtained using the optical sensor 122 and/or from the ECG signal determined using the ECG sensor 128. For another example, blood pressure can be determined from PPG and ECG signals by determining a metric of pulse wave velocity (PWV) and converting the metric of PWV to a metric of blood pressure. More specifically, a metric of PWV can be determining by determining a time from a specific feature (e.g., an R-wave) of an obtained ECG signal to a specific feature (e.g., a maximum upward slope, a maximum peak or a dicrotic notch) of a simultaneously obtained PPG signal. An equation can then be used to convert the metric of PWV to a metric of blood pressure.

In accordance with an embodiment the motion sensor 132 is an accelerometer. The accelerometer can be a three-axis accelerometer, which is also known as a three-dimensional (3D) accelerometer, but is not limited thereto. The accelerometer may provide an analog output signal representing acceleration in one or more directions. For example, the accelerometer can provide a measure of acceleration with respect to x, y and z axes. The motion sensor 132 can alternatively be a gyrometer, which provides a measure of angular velocity with respect to x, y and z axes. It is also possible that the motion sensor 132 is an inclinometer, which provides a measure of pitch, roll and yaw that correspond to rotation angles around x, y and z axes. It is also possible the user wear-able device 102 includes multiple different types of motion sensors, some examples of which were just described. Depending upon the type(s) of motion sensor(s) used, such a sensor can be used to detect the posture of a portion of a user's body (e.g., a wrist or chest) on which the user-wearable device 102 is being worn.

In the specific embodiments illustrated in FIGS. 1A, 1B and 1C the user-wearable device 102 is intended to be worn on a wrist, and thus, can be referred to as a wrist wearable device 102. FIG. 1C illustrates a rear-view of the housing or case 104 of the user-wearable device 102 according to a specific embodiment. Referring to FIG. 1C, the back of the housing or case 104, which can also be referred to as the caseback, is shown as including two metal electrodes 134a and 134b that are spaced apart from one another, two LEDs 136a and 136b and a photodiode 138.

In accordance with an embodiment, the two LEDs 136a and 136b and the photodiode 138 are components of the optical sensor 122 that was discussed above. The optical sensor 122 can alternatively include as few as one LED, or more than two LEDs. It is also possible that the optical sensor 122 includes multiple photodiodes 138. In one exemplary embodiment the optical sensor 122 includes a single LED that is surrounded by four photodiodes. Other variations are also possible and within an embodiment. The LED(s) and photodiode(s) of the optical sensor 122 are likely covered by light transmissive windows that protect the LED(s) and photodiode(s). Where such windows are in contact with the user's skin, the optical sensor 122 is considered to be in contact with the user's skin.

The two metal electrodes 134a and 134b can be used for the BIA sensor 120, the capacitive sensor 124, the GSR sensor 126 and the/or ECG sensor 128. For example, switches (not shown) can be used to selectively connect the electrode(s) 134a and/or 134b to various different electrical circuits within the housing 104 so that they can selectively function as parts of different types of sensors. More specifically, such switches can selectively connected to the two electrodes 134a and 134b to either BIA sensor circuitry, capacitive sensor circuitry, GSR sensor circuitry or ECG sensor circuitry. Where electrode(s) that are used by the BIA sensor 120, the capacitive sensor 124, the GSR sensor 126 and the/or ECG sensor 128 are in contact with the user's skin, such sensors are considered to be in contact with the user's skin.

The aforementioned sensors (except the motion sensor 132) can also be referred to as skin contact sensors. In certain embodiments, the skin contact sensors are positioned by the band 106 to contact the user's skin on their wrist. The band 106 acts as a support structure that positions the skin contact sensors against the skin on the user's wrist. In other examples, the support structure may be a bracelet, which is considered a type of band. The band, as mentioned above, can alternatively be configured to strap the housing 104 to the user's chest so that sensors and/or electrodes (of or for use by the sensors) are in contact with the skin on the user's chest. In some embodiments, the band 106 itself may include one or more skin contact sensors as well as being part of a watch. In certain embodiments, one or more of the skin contact sensors can have a slight curvature designed based on a 3D model of various wrists. As will be described in additional detail below, the skin contact sensors can be used to reliably, and in certain embodiments redundantly, detect the removal of the user-wearable device 102 from the wrist or chest of the patient.

Each of the aforementioned sensors 122, 124, 126, 128, 130, 132 can include or have associated analog signal processing circuitry to amplify and/or filter raw signals produced by the sensors. It is also noted that analog signals produced using the aforementioned sensors 122, 124, 126, 128, 130 and 122 can be converted to digital signals using one or more digital to analog converters (ADCs), as is known in the art. The analog or digital signals produced using these sensors can be subject time domain processing, or can be converted to the frequency domain (e.g., using a Fast Fourier Transform or Discrete Fourier Transform) and subject to frequency domain processing. Such time domain processing, frequency domain conversion and/or frequency domain processing can be performed by a processor (e.g., 204), or by some other circuitry.

FIG. 2 depicts an example block diagram of electrical components of the user-wearable device 102, which can include a computer system, according to an embodiment. Referring to FIG. 2, the user-wearable device 102 is shown as including a microcontroller 202 that includes a processor 204, memory 206 and a wireless interface 208. It is also possible that the memory 206 and wireless interface 208, or portions thereof, are external the microcontroller 202. The microcontroller 202 is shown as receiving signals from each of the aforementioned sensors 122, 124, 126, 128 and 130. The user-wearable device 102 is also shown as including a battery 210 that is used to power the various components of the device 102. While not specifically shown, the user-wearable device 102 can also include one or more voltage regulators that are used to step-up and or step-down the voltage provided by the battery 210 to appropriate levels to power the various components of the device 102. The memory 206 may include volatile memory (such as RAM), non-volatile memory (such as ROM, flash memory, etc.) or some combination of the two. Additional memory storage (removable and/or non-removable) may also be included.

The user-wearable device 102 is shown as including various modules, including an on-body detector module 212, a sleep detector module 214, a sleep metric module 216, a heart rate (HR) detector module 218, a heart rate variability (HRV) detector module 220, an activity detector module 222, a calorie burn detector module 224 and a authentication module 230. The various modules may communicate with one another, as will be explained below. Each of these modules 212, 214, 216, 218, 220, 222, 224 and 230 can be implemented using software, firmware and/or hardware. It is also possible that some of these modules are implemented using software and/or firmware, with other modules implemented using hardware. Other variations are also possible. In accordance with a specific embodiments, each of these modules 212, 214, 216, 218, 220, 222, 224 and 230 is implemented using software code that is stored in the memory 206 and is executed by the processor 204. The memory 206 is an example of a tangible computer-readable storage apparatus or memory having computer-readable software embodied thereon for programming a processor (e.g., 204) to perform a method. For example, non-volatile memory can be used. Volatile memory such as a working memory of the processor 204 can also be used. The computer-readable storage apparatus may be non-transitory and exclude a propagating signal.

The on-body detector module 212, which can also be referred to simply as the on-body detector 212, uses signals and/or data obtained from one or more of the above described sensors to determine whether the user-wearable device 102 is being worn by a user, as will be described in addition detail below with reference to FIGS. 7-11. Where the user-wearable device has the form factor of a wristwatch, e.g., as shown in FIGS. 1A and 1B, the on-body detector 212 may be referred to as a wrist-off detector or a wrist-on detector.

The sleep detector module 214, which can also be referred to simply as the sleep detector 212, uses signals and/or data obtained from one or more of the above described sensors to determine whether a user, who is wearing the user-wearable device 102, is sleeping. For example, signals and/or data obtained using the motion sensor 132 can be used to determine when a user is sleeping. Additionally, if the user's arm posture can be detected from the motion sensor 132, then information about arm posture can also be used to detect whether or not a user is sleeping.

The sleep metric detector module 216, which can also be referred to as the sleep metric detector 216, uses information obtained from one or more of the above described sensors and/or other modules to quantify metrics of sleep, such as total sleep time, sleep efficiency, number of awakenings, and estimates of the length or percentage of time within different sleep states, including, for example, rapid eye movement (REM) and non-REM states. The sleep metric module 216 can, for example, use information obtained from the motion sensor 132 and/or from the HR detector 218 to distinguish between the onset of sleep, non-REM sleep, REM sleep and the user waking from sleep. One or more quality metric of the user's sleep can then be determined based on an amount of time a user spent in the different phases of sleep. Such quality metrics can be displayed on the digital display 108 and/or uploaded to a base station (e.g., 252) for further analysis.

The HR detector module 218, which can also be referred to simply as the HR detector 218, uses signals and/or data obtained from the optical sensor 122 and/or the ECG sensor 128 to detect HR. For example, the optical sensor 122 can be used to obtain a PPG signal from which peak-to-peak intervals can be detected. For another example, the ECG sensor 128 can be used to obtain an ECG signal, from which peak-to-peak intervals, and more specifically R-R intervals, can be detected. The peak-to-peak intervals of a PPG signal or an ECG signal can also be referred to as beat-to-beat intervals, which are intervals between heart beats. Beat-to-beat intervals can be converted to HR using the equation HR=(1/beat-to-beat interval)*60. Thus, if the beat-to-beat interval=1 sec, then HR=60 beats per minute (bpm); or if the beat-to-beat interval=0.6 sec, then HR=100 bpm. The user's HR can be displayed on the digital display 108 and/or uploaded to a base station (e.g., 252) for further analysis.

The HRV detector module 220, which can also be referred to simply as the HRV detector 220, uses signals and/or data obtained from the optical sensor 122 and/or the ECG sensor 128 to detect HRV. For example, in the same manner as was explained above, beat-to-beat intervals can be determined from a PPG signal obtained using the optical sensor 122 and/or from an ECG signal obtained using the ECG sensor 128. HRV can be determined by calculating a measure of variance, such as, but not limited to, the standard deviation (SD), the root mean square of successive differences (RMSSD), or the standard deviation of successive differences (SDSD) of a plurality of consecutive beat-to-beat intervals. Alternatively, or additionally, obtained PPG and/or ECG signals can be converted from the time domain to the frequency domain, and HRV can be determined using well known frequency domain techniques. The user's HRV can be displayed on the digital display 108 and/or uploaded to a base station (e.g., 252) for further analysis.

The activity detector module 222, which can also be referred to simply as the activity detector 222, can determine a type and amount of activity of a user based on information such as, but not limited to, motion data obtained using the motion sensor 132, heart rate as determined by the HR detector 218, skin temperature as determined by the skin temperature sensor 130, and time of day. The activity detector module 222 can using motion data, obtained using the motion sensor 132, to determine the number of steps that a user has taken with a specified amount of time (e.g., 24 hours), as well as to determine the distance that a user has walked and/or run within a specified amount of time. Activity metrics can be displayed on the digital display 108 and/or uploaded to a base station (e.g., 252) for further analysis.

The calorie burn detector module 224, which can also be referred to simply as the calorie burn detector 222, can determine a current calorie burn rate and an amount of calories burned over a specified amount of time based on motion data obtained using the motion sensor 132, HR as determined using the HR detector 218, and/or skin temperature as determined using the skin temperature sensor 130. A calorie burn rate and/or an amount of calories burned can be displayed on the digital display 108 and/or uploaded to a base station (e.g., 252) for further analysis.

The authentication module 230 can perform an authentication determination that compares sensed biometric information of a user-wearing the user-wearable device 102, obtained using at least one of the sensors described herein, to baseline biometric information to determine whether or not they match one another. If the sensed biometric information matches the baseline biometric information, then the authentication module 230 determines that a user wearing the user-wearable device is authenticated. Alternatively, the comparison can be performed by a system that is external to the user-wearable device 102 and the authentication module can receive results of such a comparison. The authentication module 230 can also communicate with the on-body detector 212, in accordance with specific embodiments, to continually conclude (for at least a period of time) after a user is authenticated (based on a comparison between the sensed biometric information and the baseline biometric information) that the user is still authenticated without an additional comparison between additional sensed biometric information and the baseline biometric information being performed. Additional details of the operation of the authentication module, according to specific embodiments, can be appreciated from the flow diagram of FIG. 3.

The user-wearable device 102 can include less modules than shown in FIG. 2, more modules than show and/or alternative types of modules. For example, the user-wearable device 102 can also include a body water content module and/or a body fat content module that calculate the user's body water content and/or body fat percentage based on measurements obtained using the BIA sensor 120. For another example, the user-wearable device 102 can include a stress module that estimates a user's stress level based on measures obtained using the GSR sensor 126, the ECG sensor 128 and/or the skin temperature sensor 130. These are just a few examples of other types of modules or detectors that the user-wearable device 102 can have, which are not intended to be all encompassing.

The wireless interface 208 can wireless communicate with a base station (e.g., 252), which as mentioned above, can be a mobile phone, a tablet computer, a PDA, a laptop computer, a desktop computer, or some other computing device that is capable of performing wireless communication. The wireless interface 208, and more generally the user-wearable device 102, can communicate with a base station 252 using various different protocols and technologies, such as, but not limited to, Bluetooth™, Wi-Fi, ZigBee or ultrawideband (UWB) communication. In accordance with an embodiment, the wireless interface 208 comprises telemetry circuitry that include a radio frequency (RF) transceiver electrically connected to an antenna (not shown), e.g., by a coaxial cable or other transmission line. Such an RF transceiver can include, e.g., any well-known circuitry for transmitting and receiving RF signals via an antenna to and from an RF transceiver of a base station 252.

The base station 254 can also include a computer system with a memory which may include volatile and non-volatile memory components. Additional storage is available. The base station can includes one or more communication module(s) which include one or more network interfaces and transceivers which allow the base station to communicate with user-wearable device and other computer systems over wire or wirelessly or in both manners. The base station can also include input and output (I/O) devices like a display and buttons, touchscreen or a keypad, pointing device, keyboard or the like.

To avoid cluttering the drawings, a power supply and power bus or power line is not illustrated, but each of the system embodiments illustrated from a hardware perspective also includes or has access to a power supply and a power bus to which the various components using power connect for drawing power. An example of a power supply are a battery. Larger computer systems such as the base station and other networked computer systems may also have a power cord connection.

The example computer systems discussed herein include examples of computer readable storage devices. A computer readable storage device is also a processor readable storage device. Such devices may include volatile and nonvolatile, removable and non-removable memory devices implemented in any method or technology for storage of information such as computer readable instructions, data structures, program modules, software or other data. The software or instructions are used to program one or more processors to perform the methods described above Some examples of processor or computer readable storage devices are RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other device which can be used to store the information and which can be accessed by a computer.

Figure 3:
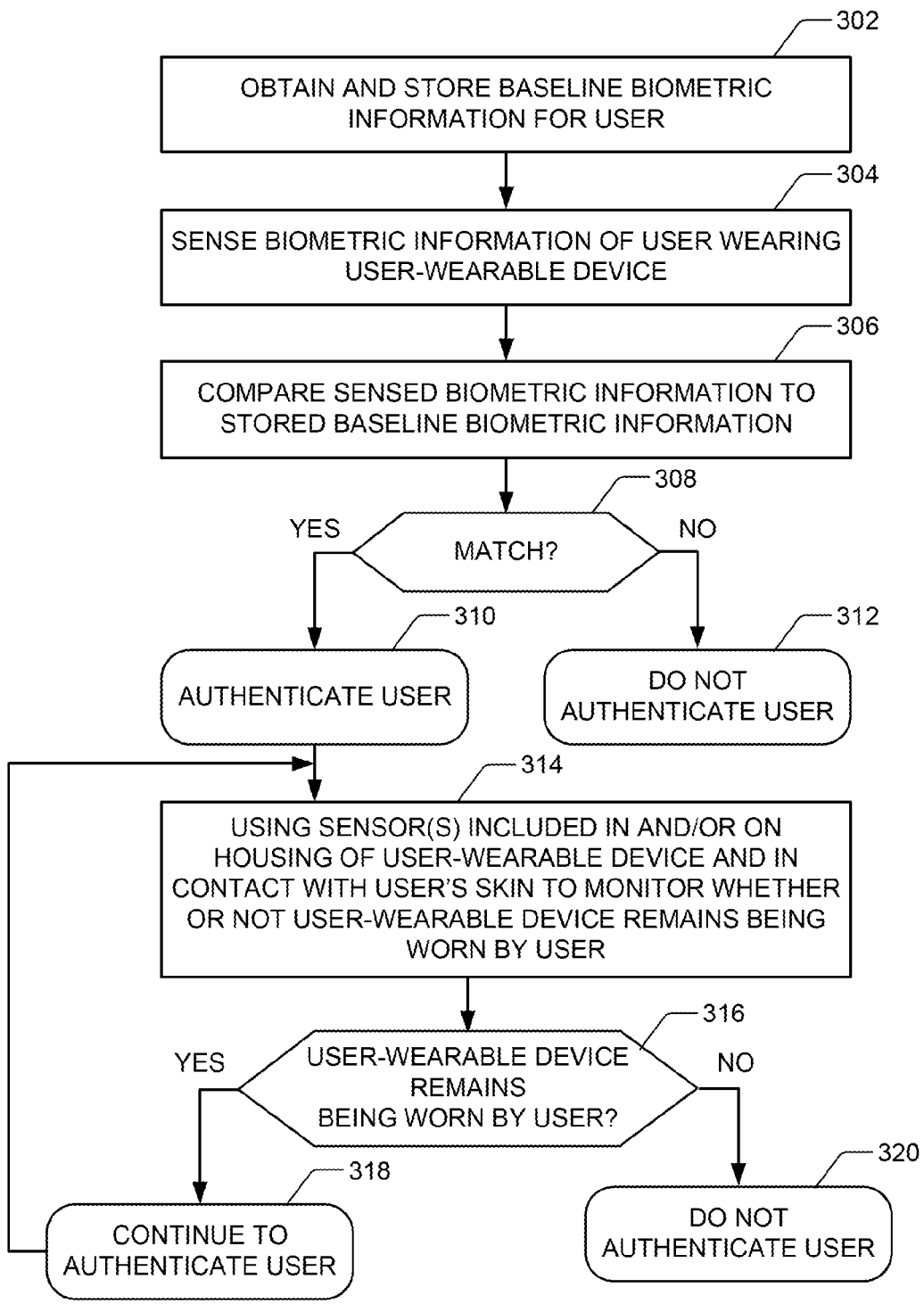
FIG. 3 is high level flow diagram used to describe methods of providing persistent authentication of a user wearing a user-wearable device according to various embodiments of the present technology.

The high level flow diagram of FIG. 3 will now be used to describe methods according to various embodiments of the present technology. Such methods, which are for use with a user-wearable device (e.g., the user-wearable device 102 described above), can be used to provide for persistent authentication of a user that is wearing the user-wearable device. Such a user-wearable device includes a housing (e.g., 104) that includes one or more sensors (e.g., 120-132) and a band (e.g., 106) that straps the housing to a portion of the user's body (e.g., the user's wrist or chest) such that at least one of the one or more sensors included in and/or on the housing is in contact with the user's skin. Where the user-wearable device relies on one or more electrodes being in contact with the user's skin in order for a sensor to sense a signal or make a measurement, the sensor is considered to be in contact with the user's skin if the electrode used by the sensor is in contact with the user's skin. An optical sensor (e.g., 122) is considered to be in contact with the user's skin if the windows for the light source and/or light detector of the optical sensor is/are in contact with the user's skin.

Referring to FIG. 3, step 302 involves obtaining and storing baseline biometric information for a user, wherein the user can be associated with a user-wearable device. A user can be associated with a user-wearable device, e.g., because they are the owner of the device, they were assigned the device, they rented the device, or for some other reason. In accordance with an embodiment, the biometric information stored at step 302 includes one or more of ECG information, PPG information and/or vein pattern information, but is not limited thereto.

In accordance with an embodiment, the baseline biometric information can be obtained at step 302 by the user-wearable device using one or more of the sensors described above. Alternatively, the baseline biometric information can be obtained at step 302 by another device or system (e.g., a client or base station device) that includes or receives information from sensors similar to the sensors described above. The obtaining and storing of baseline biometric information (which can also be referred to as reference biometric information) can occur during a registration process, which can also be referred to as an enrollment process. The purpose of the registration or enrollment process is to obtain unique biometric information for a user, so that such unique biometric information can be used at a later time to authenticate the user. The biometric information can be stored within the user-wearable device itself. If stored within the user-wearable device itself, the baseline biometric information can be encrypted and stored in secure non-volatile memory, but is not limited thereto. Alternatively, or additionally, the baseline biometric information can be stored external to the user-wearable device, e.g., in a database that is accessible by an authentication server or other system.

Figure 4A:
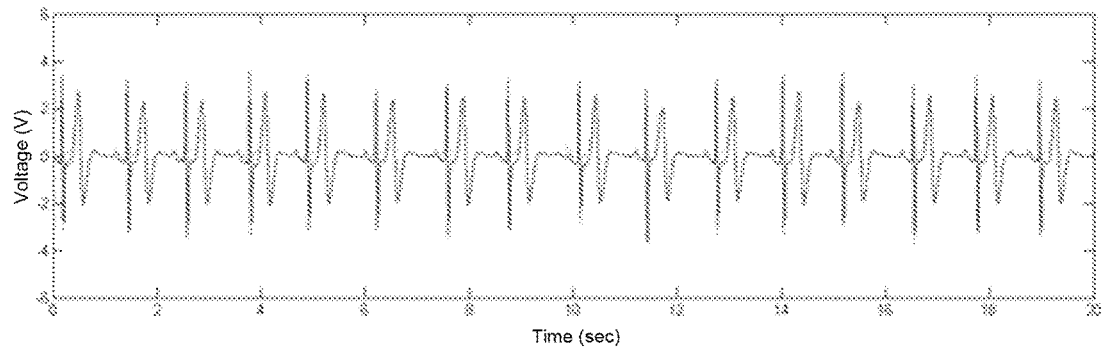
FIG. 4A illustrates an exemplary electrocardiogram (ECG) signal or trace that can be obtained using an ECG sensor of the user-wearable device introduced in FIGS. 1A-1C.
Figure 4B:
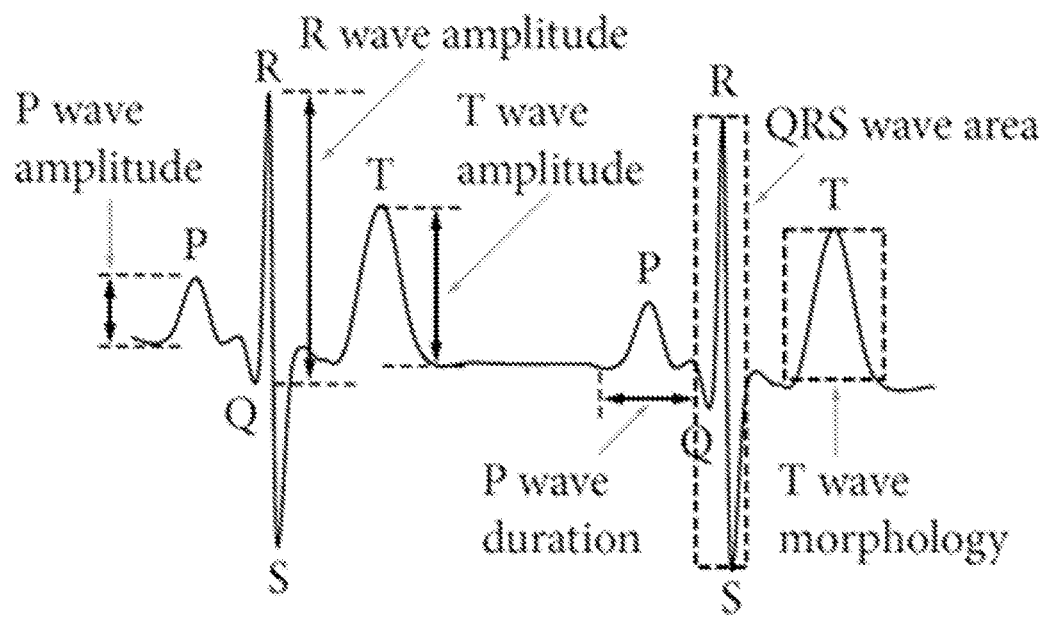
FIG. 4B illustrates exemplary ECG morphological features that can be obtained in the time domain from an ECG signal or trace, such as the one in FIG. 4A.

ECG information can be indicative of the overall morphology of one or more R-R intervals of a sensed ECG signal and/or indicative of specific morphological features or parameters of a sensed ECG signal. For example, ECG information may include an ECG signal template and/or ECG morphological features that can be obtained in the time domain. Referring briefly to FIGS. 4A and 4B, FIG. 4A illustrates an exemplary ECG signal or trace that can be obtained using an ECG sensor (e.g., 128), and FIG. 4B illustrates exemplary ECG morphological features that can be obtained in the time domain from the ECG signal or trace. In an embodiment, to extract the time domain morphological features, fiducial points can be detected first. Features such as P-wave duration, P-wave amplitude, QRS complex duration, QRS complex amplitude, R-wave duration, R-wave amplitude, T-wave duration and T-wave amplitude are examples of morphologic features that can be detected and for which ECG information can be stored. In addition to the morphological features that are found within the R-R interval, there are other features that can be found in the patterns of consecutive heart beats. Additionally, or alternatively, ECG frequency domain information can be obtained using techniques such as wavelet decomposition, Fourier transformation, or discrete cosine transform, but not limited thereto. Frequency domain features can be extracted from the results of one or more of the aforementioned transformations.

Figure 5:
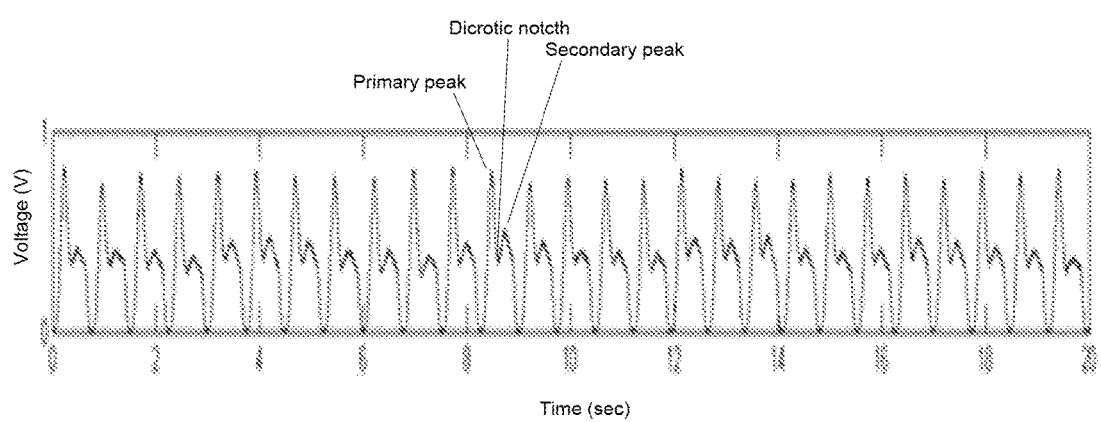
FIG. 5 illustrates an exemplary photoplethysmography (PPG) signal or trace that can be obtained using an optical sensor of the user-wearable device introduced in FIGS. 1A-1C.

PPG information can be indicative of the overall morphology of one or more cycles of a sensed PPG signal and/or indicative of specific morphological features or parameters of a sensed PPG signal. For example, PPG information may include PPG signal template and/or PPG morphological features that can be obtained in the time domain. Referring briefly to FIG. 5, illustrated therein is an exemplary PPG signal or trace that can be obtained using an optical sensor (e.g., 122). Each cycle of a PPG signal or trace include a primary pulse and a secondary pulse with a dicrotic notch therebetween. Time domain morphological features that can be extracted from a PPG signal include, e.g., amplitudes and/or durations of the primary pulse, secondary pulse and/or dicrotic notch, or ratios of selected ones of these features to one another, but are not limited thereto. Additionally, or alternatively, PPG frequency domain information can be obtained using techniques such as wavelet decomposition, Fourier transformation, or discrete cosine transform, but are not limited thereto. Frequency domain features can be extracted from the results of one or more of the aforementioned transformations.

Vein pattern information (e.g., wrist vein pattern information) can be indicative of a density of veins, vein positions, the paths or trajectories of the veins, how they branch, their diameter and/or their brightness. As explained in commonly assigned U.S. patent application Ser. No. 13/844,344, filed Mar. 15, 2013, comparing data representing a wrist vein pattern with stored reference or baseline wrist vein pattern data generated from previous detections can be used to authenticate the identity of a user with an error rate of less than one in ten thousand (1/10,000), which for many applications is sufficient. Vein pattern information can be determined using an optical sensor (e.g., 122). Additional details of an optical sensor specifically designed for sensing vein pattern information is described in the commonly assigned U.S. patent application Ser. No. 13/844,344.

Referring again to FIG. 3, at step 304 biometric information of a user wearing a user-wearable device (e.g., 102) is sensed. In accordance with specific embodiments, one or more sensors that is/are in and/or on a housing (e.g., 104) of the user-wearable device (e.g., 102) are used to perform step 304. As explained above, a band (e.g., 106) of the user-wearable device can be used to strap the housing to a portion of the user's body (e.g., the user's wrist or chest) such that at least one of the one or more sensors included in and/or on the housing is in contact with the user's skin. In accordance with embodiments, the type of biometric information that is sensed at step 304 is the same as the type of baseline biometric information that is obtained and stored at step 302.

In accordance with certain embodiments, step 304 is performed in response to the on-body detector 212 detecting that the user-wearable device was just placed onto a portion of a portion of a user's body (e.g., the user's wrist). Alternatively, or additionally, step 304 can be performed in response to some other triggering event, such as, but not limited to, a specific button being pressed by the user, or an external system requesting authentication, the user trying to access certain information, the user trying to access a certain room or area, the user trying to operate a certain machine or weapon, just to name a few.

Figure 6:
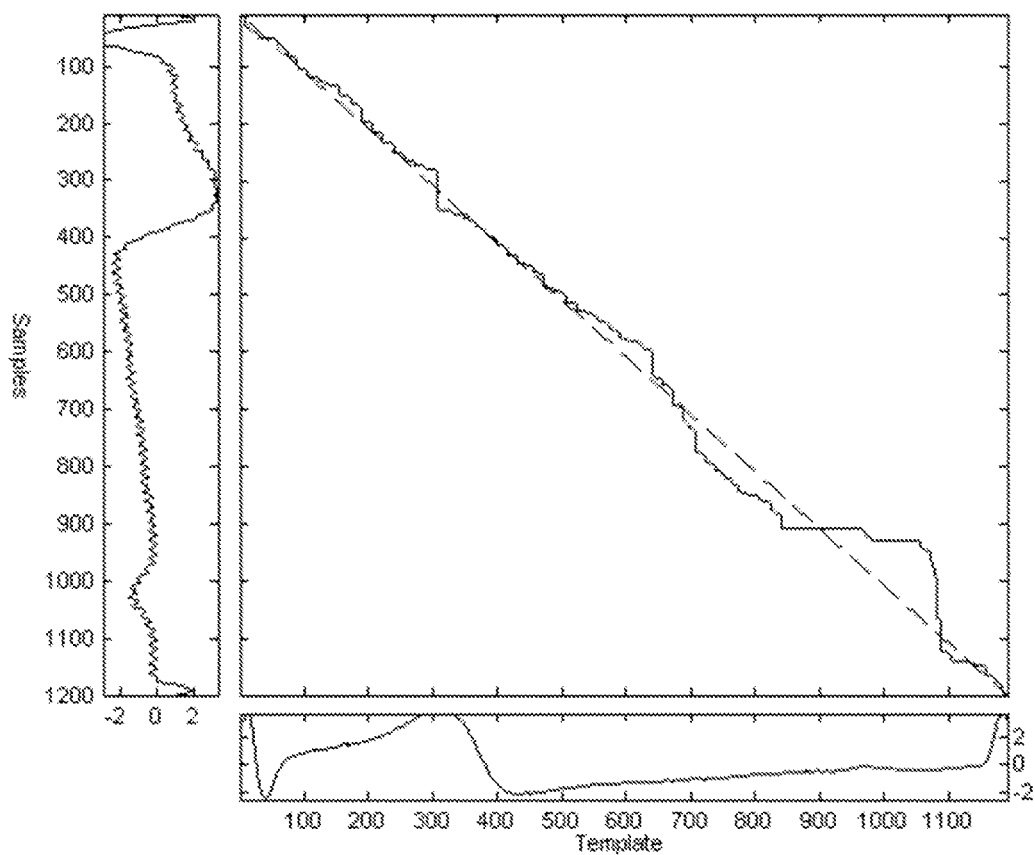
FIG. 6 graphically depicts a comparison of sensed ECG signal with a template or baseline ECG signal using dynamic time warping.

At step 306, the biometric information sensed at step 304 is compared to the baseline biometric information obtained and stored at step 302, so that there can be a determination at step 308 of whether they match one another. The sensed biometric information need not be exactly the same as the baseline information in order for there to be a match. Rather, in accordance with certain embodiments, for there to be a match between the sensed biometric information and the baseline biometric information the sensed and baseline biometric information should be similar to one another within an acceptable tolerance that can be defined as appropriate for the level of security desired. For example, if the similarity between the sensed biometric information and the baseline biometric information exceeds a specified threshold, then the sensed and baseline biometric information can be considered to match. The one or more comparisons performed at step 306 can be performed using one or more known or future developed comparison techniques, such as, but not limited to, template matching, cross-correlation, principal component analysis, dynamic time warping and/or mean square error (MSE) analysis, just to name a few. For an exemplary illustration, FIG. 6 graphically depicts a comparison of a sensed ECG signal with a template or baseline ECG signal using dynamic time warping (generated using Matlab algorithm).

In certain embodiments, the baseline biometric information and sensed biometric information that are compared to one another includes more than one of ECG, PPG and vein pattern information. For example, the biometric information can include both ECG and PPG information, which provides for increased levels of authentication. Where the biometric information includes both ECG and PPG information, the biometric information may (but need not) include information about delays or offsets between features of an ECG signal and a PPG signal, such as a time from an R-wave of an ECG signal to a primary peak of a simultaneously obtain PPG signal. For another example, the biometric information can include ECG and/or PPG information, as well as vein pattern information. Where more than one of ECG, PPG and vein pattern information is obtained, the different types of biometric information can be obtained simultaneously, or at different times.

Referring again to FIG. 3, as indicated at block 310 in FIG. 3, if there is a determination that the sensed biometric information and the baseline biometric information match, then the user is authenticated. As indicated at block 312, if there is a determination that the sensed biometric information and the baseline biometric information do not match, then the user is not authenticated.

If the user wearing the user-wearable device (e.g., 102) is authenticated, the user may be given access to certain information stored on the user-wearable device and/or certain applications or functionality performed by the user-wearable device. Additionally, or alternatively, if the user wearing the user-wearable device (e.g., 102) is authenticated, the user may be given access to certain information stored external to the user-wearable device and/or certain applications or functionality external to the user-wearable device. For other examples, if the user wearing the user-wearable device (e.g., 102) is authenticated the user may be able to use their user-wearable device to perform a financial transaction, enter a secure room or area, open a car door, and/or the like. For still more examples, if the user wearing the user-wearable device (e.g., 102) is authenticated the user may be able to operate certain machinery, vehicles, weapons and/or the like. In certain embodiments, the user-wearable device can wirelessly send to another device or system an indication that the user has been authenticated, in response to which that other device or system can grant the user to access to secure information or applications, access to a secure room or area (e.g., by unlocking a door), enable the user to complete a financial transaction (e.g., withdrawn money from an ATM), enable the user to operate certain vehicles, machinery and/or weapons, and/or the like. If the user wearing the user-wearable device (e.g., 102) is not authenticated, the user can be denied access to certain information, applications and/or functionality, can be prevented from performing certain financial transactions, and/ or can be prevented from operating certain vehicles, machinery and/or weapons, and/or the like. These are just a few examples of what can happen based on whether or not the user is authenticated, which is not intended to be all encompassing. Some other examples are discussed above and below.

The performing of steps 306, 308, 310 and 312 is an example of what can collectively be referred to as the performing of an authentication determination that compares the sensed biometric information to baseline biometric information to determine whether or not they match one another, wherein if the sensed biometric information matches the baseline biometric information the user wearing the user-wearable device is authenticated. Steps 306, 308, 310 and 312 can all be performed by the user-wearable device being worn by the user whose biometric information is sensed at step 304. Alternatively, the information sensed at step 304 can be sent (e.g., wirelessly) to a further device/system (e.g., the base station 252) that performs one or more of steps 306, 308, 310 and 312, or at least portions of one or more such steps. Where steps 306, 308, 310 and 312 are performed external to the user-wearable device, the user-wearable device may receive results of an authentication determination that compares the sensed biometric information to baseline biometric information to determine whether or not they match one another, wherein if the sensed biometric information matches the baseline biometric information the user wearing the user-wearable device is authenticated.

Still referring to FIG. 3, after determining or receiving an indication that the user wearing the user-wearable device is authenticated, at step 314 monitoring is performed to determine whether or not the user-wearable device remains being worn by the user. In accordance with specific embodiments, the monitoring at step 314 is performed using at least one of the one or more sensors included in and/or on the housing (e.g. 104) of the user-wearable device (e.g., 102) that is/are in contact with the user's skin. For example, step 314 can be performed using a BIA sensor (e.g., 120), an optical sensor (e.g., 122), a capacitive sensor (e.g., 124), a GSR sensor (e.g., 126), a skin temperature sensor (e.g., 130), or combinations thereof. Additional details of how sensors included in and/or on the housing (e.g. 104) of the user-wearable device (e.g., 102) can be used to perform the monitoring at step 314 are described in additional detail below with reference to FIGS. 7-11.

Still referring to FIG. 3, as indicated by steps 314, 316 and 318, after there is determination that the user wearing the user-wearable device is authenticated, then the user remains authenticated for at least a period of time without needing to repeat steps 304, 306, 308 and 310. In other words, for at least a period of time that the user-wearable device remains being worn by the user, it is continually concluded that the user wearing the user-wearable device is authenticated without repeating steps that involve comparing sensed biometric information to baseline information. In certain embodiments, while continually concluding that the user wearing the user-wearable device is authenticated, the method can include continually, periodically or aperiodically reporting (e.g., wirelessly) to a further device that the user is authenticated.

In accordance with an embodiment, after determining or receiving an indication that the user wearing the user-wearable device is authenticated, the user wearing the user-wearable device remains authenticated indefinitely (without repeating steps that involve comparing sensed biometric information to baseline information), so long as the user remains wearing the user-wearable device. In accordance with an alternative embodiment, after determining or receiving an indication that the user wearing the user-wearable device is authenticated, the user wearing the user-wearable device remains authenticated for a predetermined period of time (without repeating steps that involve comparing sensed biometric information to baseline information), so long as the user remains wearing the user-wearable device during the predetermined period of time. The predetermined period of time can be, e.g., 1 minute, 10 minutes, 1 hour, 1 day, but is not limited thereto. After the predetermined period of time has expired, steps 304 and 306 can be repeated to thereby determine, once again at steps 308 and 310 or 312, whether or not the user is authenticated based on a comparison between sensed biometric information and baseline information. For example, to perform this embodiment, an additional step can be added between steps 314 and 316, between steps 316 and 318, or after step 318, wherein the additional step determines whether an elapsed time since the user was authenticated (based on a comparison between sensed biometric information and baseline biometric information at step 306) exceeds the predetermined period of time. If the elapsed time does not exceed the predetermined period of time, then the user can be continually authenticated so long as they have not removed the device. If the elapsed time exceeds the predetermined period of time, then the method returns to step 304.

Referring again to step 314, it would alternatively be possible to attempt to determine whether or not the user-wearable device remains being worn by the user based on a sensor located in and/or on the band that straps the device to a portion of the user's body. For example, such a sensor may be integrated into a clasp or other connector of the band. However, for a number of reasons this is believed to be inferior to using one or more sensors included in and/or on the housing (e.g. 104) of the user-wearable device (e.g., 102) that is/are in contact with the user's skin to determine whether or not the user-wearable device remains being worn by the user. First, depending upon how tightly a user straps the band to their wrist (or other body part), the user (or a nefarious third party) may be able to slide the band off the user's wrist (or other body part) such that the user-wearable device can be removed without opening the clasp or other connector. This may enable a third party that steals the user-wearable device, or a third party that is given the user-wearable device by the initially authenticated user, to appear to be authenticated, even though they should not be authenticated. Further, it may be desirable to allow users to change the bands of their devices, e.g., for comfort reasons, style reasons, or because the band has been damaged. If a sensor that is integrated into a clasp or other connector of a band were used to detect whether or not the user-wearable device remains being worn by the user, then the band may not be removable and/or replaceable, or if removable and replaceable the user would have to replace the band with another band that is specifically designed for use with the user-wearable device. Additionally, depending upon the sophistication of a sensor integrated into a clasp or other connector of a band, it may be easy to trick the sensor into thinking that the user-wearable device has not been removed when it indeed has been removed. For example, a sensor on a clasp may be designed to indicate that the device is still being worn so long as a circuit, which is completed by closing the clasp, remains completed. Such a simple sensor can be easily tricked by connecting a wire or other electrical conductor between both ends of the clasp before opening the clasp, so that the circuit is not disconnected, even though the clasp is actually opened. For at least the above reasons, it is believed that it is superior to utilize one or more sensors included in and/or on the housing (e.g. 104) of the user-wearable device (e.g., 102) that is/are in contact with the user's skin to determine whether or not the user-wearable device remains being worn by the user.

Still referring to FIG. 3, as indicated by steps 314, 316 and 320, once it is determined that a user is no longer wearing (i.e., has removed) the user-wearable device, then the user is no longer authenticated. In certain embodiments, the method can include, after determining that the user is no longer authenticated, reporting (e.g., wirelessly) to a further device (e.g., the base station 252) that the user is not authenticated.

In accordance with an embodiment, steps 306, 308, 310, 312, 316, 318 and 320 in FIG. 3 are performed by or under control of the authentication module 230. In accordance with an embodiment, step 314 is performed by the on-body detector 212. Additional details of how sensors included in and/or on the housing (e.g. 104) of the user-wearable device (e.g., 102) can be used to perform the monitoring at step 314 will now be described with reference to FIGS. 7-11. In accordance with certain embodiments, the steps described with reference to FIGS. 7-11 can be performed by the on-body detector 212.

Figure 7:
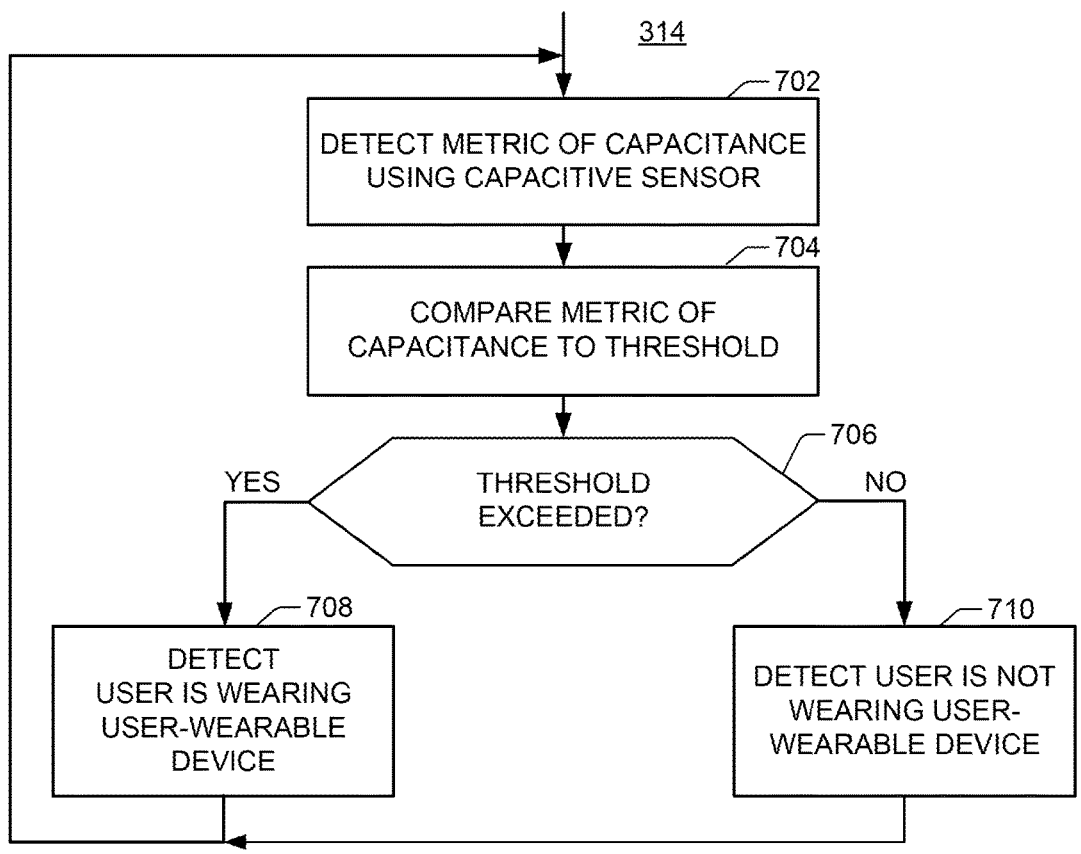
FIG. 7 is a high level flow diagram that provides additional details of one of the steps introduced in FIG. 3 that involves using a capacitive sensor to determine whether or not a user is wearing a user-wearable device.

FIG. 7 will now be used to describe a technique for using the capacitive sensor 124 to detect whether or not a user is still wearing the user-wearable device 102. Referring to FIG. 7, at step 702 a metric of capacitance is obtaining using the capacitive sensor 124, wherein the closer an object (e.g., the user's wrist or chest) is to the electrode of the capacitive sensor 124, the greater the capacitance. Depending upon how the capacitive sensor 124 is implemented, the amplitude of an oscillating signal or a frequency of an oscillating signal increases with increases in capacitance, and thus, with reduction in distance between the capacitive sensor 124 and an object (e.g., the user's wrist or chest). Accordingly, the metric of capacitance obtained at step 702 can be a measure of amplitude or frequency, but is not limited thereto. At step 704 the metric of capacitance is compared to an appropriate capacitive threshold. If there is a determination at step 706 that the threshold is exceed, then there is a detection at step 708 that the user-wearable device is being worn by a user. If the threshold is not exceeded, as determined at step 706, then there is a detection at step 710 that the user-wearable device is not being worn by a user. The capacitive threshold can be predefined, or can be specified based on a metric of capacitance determined using the capacitive sensor 124 when the user was initially authenticated. For example, before, during or after step 304 (in FIG. 3), a metric of capacitance can be measured, and the capacitive threshold can be set equal to that measured metric of capacitance plus and/or minus some tolerance. It would also be possible to use a capacitive threshold range, instead of a single capacitive threshold.

Figure 8:
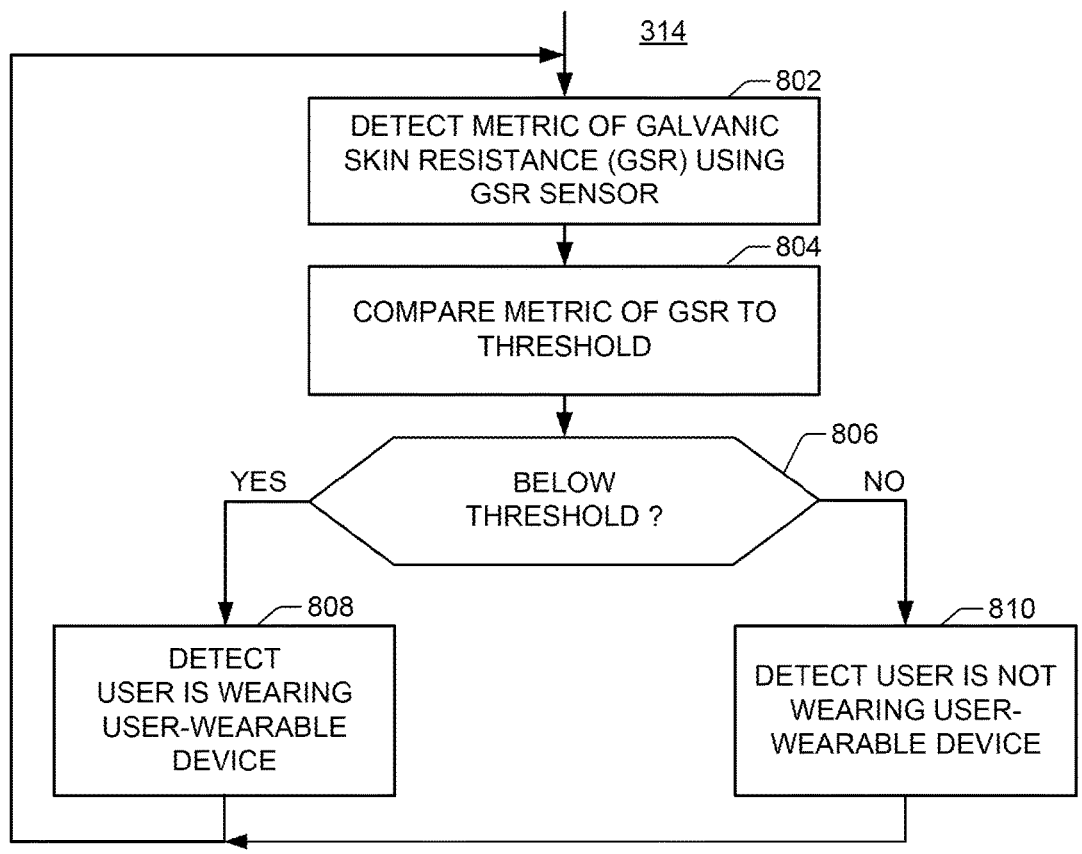
FIG. 8 is a high level flow diagram that provides additional details of one of the steps introduced in FIG. 3 that involves using a galvanic skin resistance sensor to determine whether or not a user is wearing a user-wearable device.

FIG. 8 will now be used to describe a technique for using the GSR sensor 126 to detect whether or not a user is still wearing the user-wearable device 102. Referring to FIG. 8, at step 802 a metric of galvanic skin resistance (GSR) is obtaining using the GSR sensor 126. The GSR will be relatively low when the GSR sensor 126 is in contact with a user's skin, and will be relatively high when the GSR sensor 126 is not in contact with a user's skin. At step 804 the metric of GSR is compared to an appropriate GSR threshold. If there is a determination at step 806 that the GSR metric is below the threshold, then there is a detection at step 808 that the user-wearable device is being worn by a user. If the GSR metric is not below the threshold, as determined at step 806, then there is a detection at step 810 that the user-wearable device is not being worn by a user. The GSR threshold can be predefined, or can be specified based on a metric of GSR determined using the GSR sensor 126 when the user was initially authenticated. For example, before, during or after step 304 (in FIG. 3), a metric of GSR can be measured, and the GSR threshold can be set equal to that measured metric of GSR plus and/or minus some tolerance. It would also be possible to use a GSR threshold range, instead of a single GSR threshold.

Figure 9:
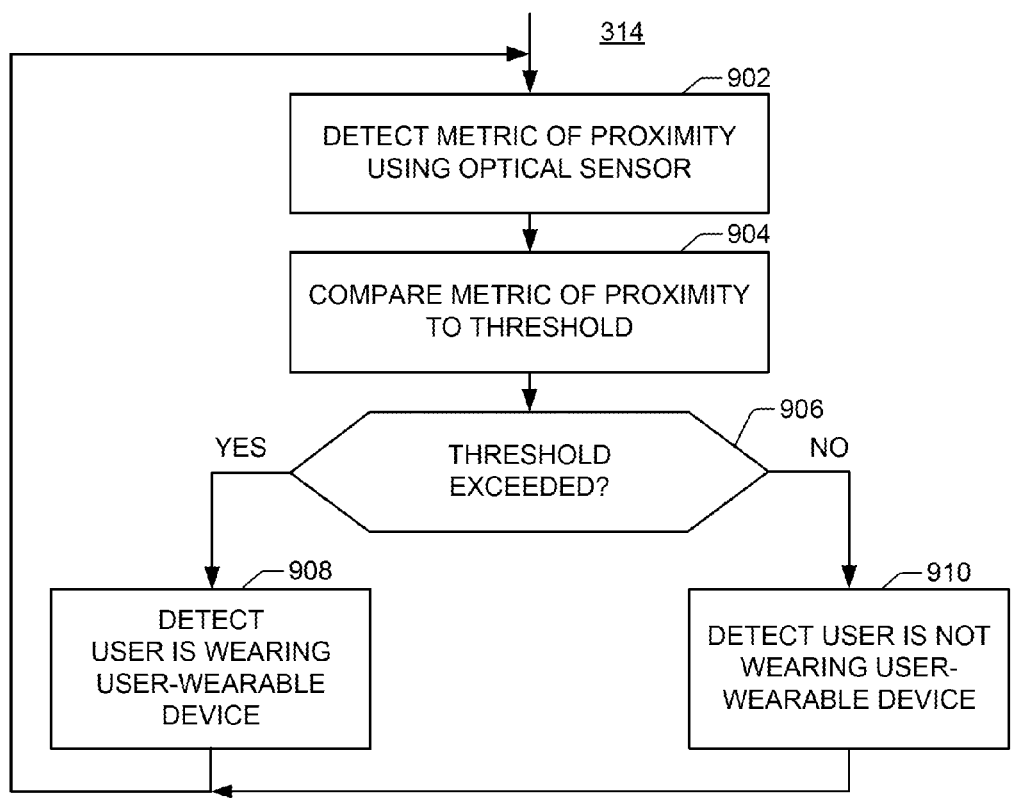
FIG. 9 is a high level flow diagram that provides additional details of one of the steps introduced in FIG. 3 that involves using an optical sensor configured as a proximity sensor to determine whether or not a user is wearing a user-wearable device.

FIG. 9 will now be used to describe a technique for using the optical sensor 122 to detect whether or not a user is still wearing the user-wearable device 102, wherein the optical sensor includes a light source and a light detector that collective operate as an optical proximity detector. Referring to FIG. 9, at step 902 a metric of proximity is obtaining using the optical sensor 122. The metric of proximity can be the amplitude of the signal produced by the light detector of the optical sensor 122, in response to light being emitted by the light source of the optical sensor 122 and reflected from the user's skin and incident on the light detector. Alternatively, or additionally, the metric of proximity can be the phase offset of the signal produced by the light detector of the optical sensor 122 (in response to light being emitted by the light source of the optical sensor 122 and reflected from the user's skin and incident on the light detector) relatively to the phase of the light emitted by the light source of the optical sensor. At step 904 the metric of proximity is compared to an appropriate proximity threshold. If there is a determination at step 906 that the metric of proximity is above the threshold, then there is a detection at step 908 that the user-wearable device is being worn by a user. If the metric of proximity is not above the threshold, as determined at step 906, then there is a detection at step 910 that the user-wearable device is not being worn by a user. The proximity threshold can be predefined, or can be specified based on a metric of proximity determined using the optical sensor 122 when the user was initially authenticated. For example, before, during or after step 304 (in FIG. 3), a metric of proximity can be measured, and the proximity threshold can be set equal to that measured metric of proximity plus and/or minus some tolerance. It would also be possible to use a proximity threshold range, instead of a single proximity threshold.

Figure 10:
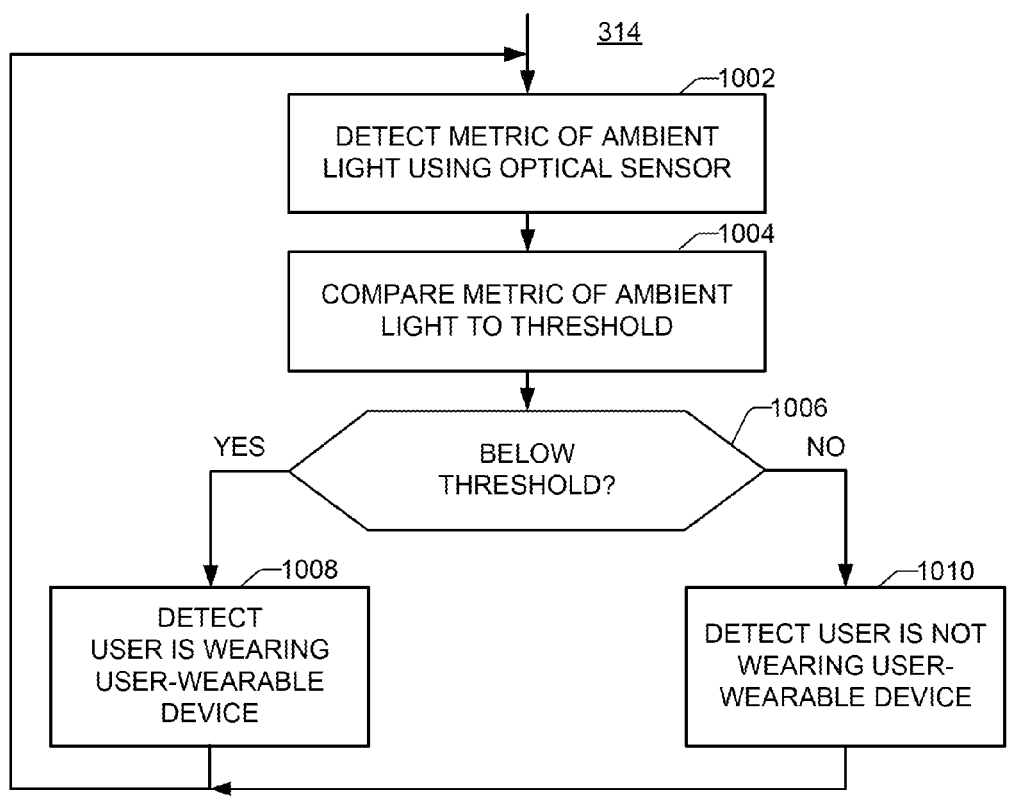
FIG. 10 is a high level flow diagram that provides additional details of one of the steps introduced in FIG. 3 that involves using an optical sensor configured as an ambient light sensor to determine whether or not a user is wearing a user-wearable device

FIG. 10 will now be used to describe a technique for using the optical sensor 122 to detect whether a user is wearing the user-wearable device 102, wherein the optical sensor 122 includes a light detector that operates as an ambient light sensor that will be at least substantially covered when a user is wearing the user-wearable device 102. More specifically, because the optical sensor 122 is placed against a user's skin when a user is wearing the user-wearable device 102, substantially no ambient light should reach the light sensor. Referring to FIG. 10, at step 1002 an ambient light metric is obtaining using the optical sensor 122. The ambient light metric can be the amplitude of the signal produced by the light detector of the optical sensor 122 that is operating as an ambient light sensor. At step 1004 the metric of ambient light is compared to an appropriate ambient light threshold. If there is a determination at step 1006 that the metric of ambient light is below the threshold, then there is a detection at step 1008 that a user is wearing the user-wearable device. If the metric of ambient light is not above the threshold, as determined at step 1006, then there is a detection at step 1010 that a user is not wearing the user-wearable device. The ambient light threshold can be predefined, or can be specified based on a metric of ambient light determined using the optical sensor 122 when the user was initially authenticated.

For example, before, during or after step 304 (in FIG. 3), a metric of ambient light can be measured, and the ambient light threshold can be set equal to that measured metric of ambient light plus and/or minus some tolerance. It would also be possible to use a ambient light threshold range, instead of a single ambient light threshold.

Figure 11:
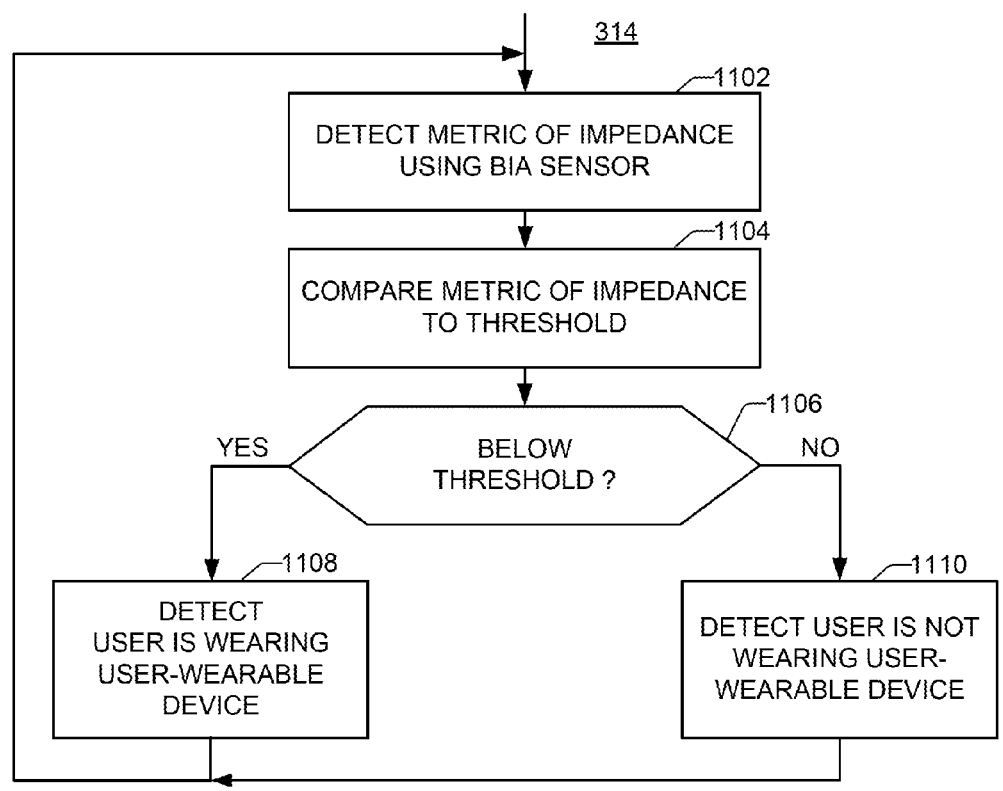
FIG. 11 is a high level flow diagram that provides additional details of one of the steps introduced in FIG. 3 that involves using a bioimpedance analysis sensor to determine whether or not a user is wearing a user-wearable device.

FIG. 11 will now be used to describe a technique for using the BIA sensor 120 to detect whether or not a user is still wearing the user-wearable device 102. Referring to FIG. 8, at step 1102 a metric of impedance is obtaining using the BIA sensor 120. The impedance will be relatively low when the BIA sensor 120 is in contact with a user's skin, and will be very high when the BIA sensor 120 is not in contact with a user's skin. At step 1104 the metric of impedance is compared to an appropriate impedance threshold. If there is a determination at step 1106 that the impedance metric is below the threshold, then there is a detection at step 1108 that the user-wearable device is being worn by a user. If the impedance metric is not below the threshold, as determined at step 1106, then there is a detection at step 1110 that the user-wearable device is not being worn by a user. The impedance threshold can be predefined, or can be specified based on a metric of impedance determined using the BIA sensor 120 when the user was initially authenticated. For example, before, during or after step 304 (in FIG. 3), a metric of impedance can be measured, and the impedance threshold can be set equal to that measured metric of impedance plus and/or minus some tolerance. It would also be possible to use an impedance threshold range, instead of a single impedance threshold.

It is also possible that combinations of the embodiments described above with reference to FIGS. 7-11 can be used to detect whether or not a user is wearing or still wearing the user-wearable device 102. In other words, more than one of the above described sensors can be used to detect whether or not a user is wearing the user-wearable device 102. Where multiple different techniques/sensors are used for detecting whether or not a user is wearing or still wearing the user-wearable device 102, the different techniques can be performed in parallel and/or serially. The use of multiple different techniques/sensors for detecting whether or not a user is wearing or still wearing the user-wearable device 102, and thus whether the user is continually authenticated, provides for redundancy that increases the level of authentication by making it more difficult to trick the device.

In accordance with an embodiment, the optical sensor 122 and/or the capacitive sensor 124 can also be used by the on-body detector 212 to detect when the user-wearable device is being worn by a user, but is being worn more loosely than preferred such that one or more sensors operate in a less than optimal manner, or in a manner that does not enable the user to be acceptably authenticated. Preferably, the sensors on the backside of the housing 104 should be in contact with a patient's skin to operate in their optimal manner. If not in contact with the skin, signals produced by one or more of the sensors may be noisy and/or inaccurate. As explained herein, the on-body detector 212 can compare signals or metrics produced using sensors to corresponding thresholds to determine whether or not the user-wearable device 102 is being worn by a user. Further thresholds can be used to determine if the device 102, even though being worn, is being worn more loosely than preferred, e.g., such that the sensors do not sufficiently contact the user's skin. Where the on-body detector 212 detects that the user-wearable device 102 is being worn more loosely than preferred, the user can be instructed, e.g., via a message displayed on the display 108, that they should tighten or otherwise adjust the device 102 such that the device 102 is in better contact with the user's skin. In accordance with certain embodiments, a user will not be authenticated when it is determined that the user-wearable device 102 is being worn too loosely.

In accordance with certain embodiments, persistent authentication relies on a user-wearable device continuously being on the user's wrist or chest after an authentication based on a comparison between sensed and baseline biometric information is made. This allows the device to conclude or declare that the wearer's identity is validated. A substantially fail-safe, redundant method of detecting the removal of the device from the wrist is therefore, an element of certain embodiments of the present technology. When the device is removed from the wrist or chest, the device will no longer conclude or declare authentication or validation of identity. In accordance with certain embodiments, to establish authentication, the device needs to be placed on the wrist or chest and the validation measurements needs to be taken. In certain embodiments, for more critical authentication or identity validation applications, the system can request the user to provide real time ECG and PPG signals at the time of a transaction. In accordance with certain embodiments, entry of a correct password (e.g., using a touch screen display of the user-wearable device) can also be required.

The sensor based persistent authentication techniques described herein can be used for a large number of applications, many of which were already described above, and further ones of which will now be described. One benefit is to provide irrefutable authentication of the identity of the owner of a token (electronic key). Some additional benefits are (1) enabling of transactions: Transactions based on 2D barcode, NFC, BLE, or other means of communication can be enabled based on the authentication of the wearer; (2) Validation of exercises: Authentication allows verification of the wearer and thus provides evidence that the person receiving the credit for the exercise (e.g. for health insurance or corporate wellness programs) is the authorized person; (3) Access to devices and appliances: Access to laptops, phones, workstation, etc. can be based on persistent authentication; and (4) Access to restricted areas: The addition of persistent authentication to a token (e.g. RFID) provides additional level of security, ensuring that that only the authorized and designated of the token accesses the restricted area. This could be used for secured areas but could also be used for access to paid facilities.

Referring back to FIG. 2, in accordance with certain embodiments, a radio communication range between the user-wearable device 102 and the base station 252 may be engineered to provide a well-defined region of operation. Since the user-wearable device, e.g., a wrist worn device, is physically bound to the user, the limited radio range of the device 102 ensures that the user is within a secured limited region around the base station. When the communication link between the base station and the wearable device is broken, the base station recognizes that the user is absent and notifies one or more applications requesting authentication. For example, an application executing on the base station 252 (or another computer system in communication with the base station 254) may cut off access to sensitive data. An identifier token may be used to establish a communication link between the user-wearable device and the base station 254.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto. While various embodiments have been described above, it should be understood that they have been presented by way of example, and not limitation. It will be apparent to persons skilled in the relevant art that various changes in form and detail can be made therein without departing from the spirit and scope of the invention. The breadth and scope of the present invention should not be limited by any of the above-described exemplary embodiments, but should be defined only in accordance with the following claims and their equivalents.

What is claimed is:

1. A method for persistent authentication of a user, comprising
   (a) sensing photoplethysmography (PPG) information of a user wearing a user-wearable device,
      the user-wearable device including a housing that includes an optical sensor and a band that is configured to strap the housing to a portion of the user's body such that the optical sensor included in and/or on the housing is in contact with the user's skin, and
      the sensing performed using the optical sensor of the user-wearable device;
   (b) performing or receiving results of an authentication determination that compares the sensed PPG information to baseline PPG information to determine whether or not they match one another, wherein if the sensed PPG information matches the baseline PPG information then the user wearing the user-wearable device is authenticated;
   (c) after determining or receiving an indication that the user wearing the user-wearable device is authenticated, monitoring whether or not the user-wearable device remains being worn by the user,
      the monitoring performed using the optical sensor included in and/or on the housing and in contact with the user's skin, which is the same optical sensor used for sensing the PPG information that is compared to the baseline PPG information as part of the authentication determination;
   (d) after determining or receiving an indication that the user wearing the user-wearable device is authenticated, for a predetermined period of time that the user-wearable device remains being worn by the user continually concluding that the user wearing the user-wearable device is authenticated without repeating steps (a) and (b); and
      after the predetermined period of time repeating steps (a) through (d).

2. The method of claim 1, wherein at step (c), in addition to performing the monitoring using the same optical sensor used for sensing the PPG information as part of the authentication determination, the monitoring is also performed using one or more additional sensors included in and/or on the housing of the user-wearable device that is/are selected from a group consisting of a capacitive sensor and a galvanic skin resistance sensor.

3. The method of claim 1, further comprising:
   after determining or receiving an indication that the user wearing the user-wearable device is authenticated, wirelessly reporting to a further device that the user is authenticated.

4. The method of claim 3, further comprising:
   while continually concluding that the user wearing the user-wearable device is authenticated, continually, periodically or aperiodically wireless reporting to the further device that the user is authenticated.

5. The method of claim 1, further comprising:
   (e) after determining or receiving an indication that the user wearing the user-wearable device is authenticated, determining that the user is no longer authenticated in response to detecting that the user is no longer wearing the user-wearable device.

6. The method of claim 5, further comprising:
   (f) after determining that the user is no longer authenticated, wireless reporting to a further device that the user is not authenticated.

7. The method of claim 1, further comprising:
   determining or receiving an indication that the user wearing the user-wearable device is not authenticated if the sensed PPG information does not match the baseline PPG information; and
   after determining or receiving an indication that the user wearing the user-wearable device is not authenticated, wirelessly reporting to a further device that the user is not authenticated.

8. The method of claim 1,
   further comprising, prior to step (a), storing the baseline PPG information within non-volatile memory of the user-wearable device; and
   wherein step (b) comprises performing the authentication determination, the performing performed by the user-wearable device.

9. The method of claim 1, wherein the baseline PPG information is stored external to the user-wearable device, the method further comprising:
   after step (a), sending the sensed PPG information to a system external to the user-wearable device so that the system external to the user-wearable device can compare the sensed PPG information, stored external to the user-wearable device, to the baseline PPG information to perform the authentication determination;
   wherein step (c) comprises receiving results of the authentication determination from the system external to the user-wearable device.

10. A method for persistent authentication of a user, comprising
   (a) sensing biometric information of a user wearing a user-wearable device,
      the user-wearable device including a housing that includes one or more sensors and a band that is configured to strap the housing to a portion of the user's body such that at least one of the one or more sensors included in and/or on the housing is in contact with the user's skin, and
      the sensing performed using at least one of the one or more sensors of the user-wearable device;
   (b) performing or receiving results of an authentication determination that compares the sensed biometric information to baseline biometric information to determine whether or not they match one another, wherein if the sensed biometric information matches the baseline biometric information the user wearing the user-wearable device is authenticated;

(c) after determining or receiving an indication that the user wearing the user-wearable device is authenticated, monitoring whether or not the user-wearable device remains being worn by the user, the monitoring performed using at least one of the one or more sensors of the user-wearable device;

d) after determining or receiving an indication that the user wearing the user-wearable device is authenticated, for a predetermined period of time that the user-wearable device remains being worn by the user continually concluding that the user wearing the user-wearable device is authenticated without repeating steps (a) and (b); and after the predetermined period of time repeating steps (a) through (d).

11. The method of claim 10, wherein at step (c), after determining or receiving an indication that the user wearing the user-wearable device is authenticated, monitoring whether or not the user-wearable device remains being worn by the user using a capacitive sensor.

12. The method of claim 10, wherein at step (c), after determining or receiving an indication that the user wearing the user-wearable device is authenticated, monitoring whether or not the user-wearable device remains being worn by the user using a galvanic skin resistance sensor.

13. A user-wearable device, comprising:
a housing;
a band configured to strap the housing to a portion of a user's body;
an optical sensor in and/or on the housing and configured to be in contact with a user's skin when the band straps the housing to a portion of a user's body, and wherein the optical sensor that contacts a user's skin is configured to sense photoplethysmography (PPG) information of a user that is wearing the user-wearable device;
a processor configured to perform or receive results of an authentication determination that compares sensed PPG information, obtained using the optical sensor, to baseline PPG information to determine whether or not they match one another, wherein if the sensed PPG information matches the baseline PPG information a user wearing the user-wearable device is authenticated; and
the processor also configured to use the same optical sensor, which is used to sense the PPG information that is used by the authentication module to determine whether the user wearing the user-wearable device is authenticated, to determine whether or not the user-wearable device is being worn by a user;
wherein after the user is authenticated based on a comparison between the sensed PPG information and the baseline PPG information, the processor is configured to continually conclude that the user is authenticated for a predetermined period of time, without an additional comparison between additional sensed PPG information and the baseline PPG information being performed, if the processor detects that the user-wearable device is still being worn by the user; and
wherein, after the predetermined period of time, the processor is configured to perform or receive results of a further authentication determination that compares further sensed PPG information, obtained using the optical sensor, to the baseline PPG information to determine whether or not they match one another.

14. The user-wearable device of claim 13, further comprising at least one of a capacitive sensor or a galvanic skin resistance sensor in and/or on the housing and configured to be in contact with a user's skin when the band straps the housing to a portion of a user's body, and wherein the processor is configured to also use at least one of the capacitive sensor or the galvanic skin resistance sensor to determine whether or not the user-wearable device is being worn by a user.

15. The user-wearable device of claim 13, wherein after the processor determines or receives an indication that the user wearing the user-wearable device is authenticated, the processor is configured to continually conclude that the user wearing the user-wearable device is authenticated for as long as the processor determines that the user-wearable device remains being worn by the user.

16. The user-wearable device of claim 15, wherein:
after the processor determines or receives an indication that the user wearing the user-wearable device is authenticated, the processor is configured to continually conclude that the user wearing the user-wearable device is authenticated for a predetermined period of time that the processor determines that the user-wearable device remains being worn by the user.

17. The user-wearable device of claim 13, further comprising:
a wireless interface configured to wirelessly report to another device whether or not the user is authenticated.

18. The user-wearable device of claim 17, wherein while the processor continually concludes that the user wearing the user-wearable device is authenticated, the wireless interface continually, periodically or aperiodically wireless reports to a further device that the user is authenticated.

* * * * *